(12) United States Patent
Hoek (10) Patent No.: US 6,692,446 B2
(45) Date of Patent: Feb. 17, 2004

(54) PASSIVE BIOTELEMETRY

(75) Inventor: Bertil Hoek, Vasteras (SE)

(73) Assignee: Radi Medical Systems AB, Uppsala (SE)

( * ) Notice: Subject to any disclaimer, the term of this patent is extended or adjusted under 35 U.S.C. 154(b) by 165 days.

(21) Appl. No.: 09/811,830

(22) Filed: Mar. 20, 2001

(65) Prior Publication Data

US 2001/0045899 A1 Nov. 29, 2001

Related U.S. Application Data

(60) Provisional application No. 60/199,360, filed on Apr. 25, 2000.

(30) Foreign Application Priority Data

Mar. 21, 2000 (EP) ............................................. 0850050

(51) Int. Cl.⁷ ............................ A61B 5/00; A61M 25/00
(52) U.S. Cl. ........................................ 600/585; 600/300
(58) Field of Search ................................. 600/300, 301, 600/372, 481, 483, 486, 500, 509, 544, 546, 433–435, 549, 561, 585, 587; 128/897–899, 903, 904

(56) References Cited

U.S. PATENT DOCUMENTS

| | | | |
|---|---|---|---|
| 3,853,117 A | | 12/1974 | Murr |
| 4,026,276 A | | 5/1977 | Chubbuck |
| RE35,648 E | * | 11/1997 | Tenerz et al. ............... 600/374 |
| 5,704,352 A | * | 1/1998 | Tremblay et al. ........... 600/300 |
| 6,053,873 A | * | 4/2000 | Govari et al. ............... 600/462 |
| 6,132,371 A | * | 10/2000 | Dempsey et al. ........... 600/300 |
| 6,201,980 B1 | * | 3/2001 | Darrow et al. .............. 600/345 |
| 6,261,247 B1 | * | 7/2001 | Ishikawa et al. ............ 600/587 |
| 6,312,380 B1 | * | 11/2001 | Hoek et al. .................. 600/437 |
| 6,369,712 B2 | * | 4/2002 | Letkomiller et al. ...... 340/425.5 |
| 6,517,481 B2 | * | 2/2003 | Hoek et al. .................. 600/300 |

OTHER PUBLICATIONS

Robert Puers, "Linking Sensors With Telemetry: Impact On The System Design", Transducers (1995), vol 1, pp. 47–50.
Samaun et al. "An IC Piezoresistive Pressure Sensor for Biomedical Instrumentation", IEEE Transactions On Biomedical Engineering, vol. BME–20, No. 2, Mar. 1973.
Craig S. Sander et al. "A Monolithic Capacitive Pressure Sensor with Pulse–Period Output", IEEE Transactions On Electron Devices, vol. ED–27, No. 5, May 1980.

* cited by examiner

*Primary Examiner*—Charles Marmor
(74) *Attorney, Agent, or Firm*—Foley & Lardner (57) ABSTRACT

A method and a device for measuring a physiological variable in a living body, whereby a transmitter (1) is disposed outside of the body to transmit radio frequent energy, and a receiver (3) of radio frequent energy is disposed outside of the body. A transponder unit (2), having a sensor (11) sensitive to the physical variable, and a modulator unit (12) for controlling the radio frequent energy absorption of the transponder unit according to a time-sequence representing said physical variable, is introduced into the body. The transmitter sends radio frequent energy of substantially constant frequency and amplitude onto the transponder, and the receiver monitors the radio energy absorption of the transponder unit to determine the time-sequence representing said physical variable. The time-sequence is decoded to interpret it as a measure of the physical variable.

18 Claims, 5 Drawing Sheets

PASSIVE BIOTELEMETRY

The Applicant hereby claims the benefit of priority of U.S. Provisional Application 60/199,360, filed Apr. 25, 2000, and European Application 00850050.6, filed Mar. 1, 2000. The entire contents of both of these applications is incorporated herein by reference.

TECHNICAL FIELD OF THE INVENTION

The present invention relates to a device and a method for wireless transferring of information on physiological variable values, and especially of such information that has been determined by invasive measurements.

BACKGROUND OF THE INVENTION

There is a general need for invasive measurements of physiological variables. For example, when investigating cardiovascular diseases it is strongly desired to obtain local measurements of pressure and flow in order to evaluate the condition of the subject.

Therefore, methods and devices have been developed for disposing a miniature sensor at the location where the measurements should be performed, and for communicating with the miniature sensor.

For example, a system and a method for measuring fluid pressure of a living body is described in U.S. Pat. No. 3,853,117. A sensor for implantation in the cranial cavity is formed as a mechanically resonant structure, the resonant frequency being a function of the fluid pressure. By applying sonic energy from an external source, and by receiving the responding resonance signal, it is possible it is possible to detect the resonance frequency, and consequently to determine the pressure of the fluid.

Another example of a known intracranial pressure monitor is known through U.S. Pat. No. 4,026,276, wherein is described an apparatus including a passive resonant circuit having a natural frequency influenced by ambient pressure. The local pressure is measured by observation of the frequency at which energy is absorbed from an imposed electromagnetic field located externally of the cranium.

In order to communicate the measured representation of the physiological variable devices based on acoustical as well as electromechanical interaction have been developed. In both cases, the sensor comprises a resonance element, its resonance frequency being a function of the physiological variable to be determined. Energy is radiated towards the resonance element from an external transmitter of acoustical or electromagnetic waves, respectively. The frequency of the transmitted energy is swept over a pre-selected range, and is registered by a monitoring unit. During the frequency sweep the registering unit will detect the resonance frequency of the resonance element, since a drop of the monitored transmitted energy will occur at this frequency.

Both of the examples above of known devices for invasive measurements of physiological variables are examples of passive systems, i.e. the sensor inside the body does not require a source of energy, such as a battery or electricity provided via electrical leads.

For guiding a sensor to a specific point of measurement during investigating cardiovascular diseases it is known to mount a miniature sensor at the distal end of a guide wire or a catheter. The guide wire or the catheter is inserted into a blood vessel such as the femoral artery, and is guided by fluoroscopy to local sites within the cardiovascular system where improper functioning is suspected.

The development of miniature sensors, or micro-sensors, for a number of physiological variables, including pressure, flow, temperature etc., constitutes a historical landmark.

However, the assembly of the sensor and the associated cables and connectors is difficult to perform in a cost-efficient manner due to the small physical dimensions, the required mechanical precision and uncompromisable demands on patient safety. More specifically, it is estimated that about half the cost, or more, of the total manufacturing cost for such devices are traceable to connectors and cables.

As a consequence, devices performing these functions are still expensive, and the spread of their use is limited to areas of highest clinical priority. The cost aspect is further emphasised by the fact that devices for invasive procedures must be regarded as disposable items, due to the risk of transmitting infectious diseases. If the cost of cables and connectors could be minimised or even eliminated, large savings would be possible.

Another problem with passive sensors of the kind disclosed in U.S. Pat. No. 4,026,276 is the undesired electromagnetic coupling between the transmitter/receiver in the one hand, and the sensor on the other hand. This coupling is due to the fact that the power supply and the signal transmission are not functionally separated. A manifestation of this problem is that the output signal of the system is influenced by the position of the sensor, which obviously is an undesired property.

This problem could be overcome by adding active electronic circuitry to the sensor, including a local transmitter operating at a frequency other than the frequency used for providing electric power to the sensor and the circuitry. Thereby, the function of wireless power supply should be separated from that of signal transmission and, consequently, the output signal should not be influenced by the position of the sensor. Such a solution has been described by R. Puers, "Linking sensors with telemetry: Impact on the system design", Proc. $8^{th}$ Int. Conf. Solid State Sensors and Actuators, Transducers-95, Stockholm Sweden, Jun. 25–29, 1995, Vol 1, pp 47–50. However, a drawback of this solution is that it is difficult to miniaturise to the size desired for medical use with a guide wire. Furthermore, wideband systems of this kind are amenable to electromagnetic interference and disturbances.

Thus, there is a need for an improved communication system for communication with a sensor positioned inside a body of a subject for invasive measurement of a physiological variable, said communication system exhibiting reduced sensitivity to the position of the sensor as well as to electromagnetic interference.

SUMMARY OF THE INVENTION

It is the object of the present invention to provide a device for overcoming the problem referred to above.

This object is achieved with a passive biotelemetry system according to claim 1 of the appended claims.

According to the invention, an electronic circuit forming a transponder unit is provided that may be integrated on a single silicon die of extremely small dimensions, and requires only a small number of discrete components which all can be accommodated and packaged within the available space of a guide wire having an outside diameter of 0.4 mm, or on a separate plate for implantation. Alternatively, the transponder unit could be inserted into a living body as an implant.

The system operates at a low bandwidth and hence is not sensitive to electromagnetic disturbances. Neither is it sensitive to position, nor to the precise control of the transmission properties of the medium.

Furthermore, it eliminates the requirement of cables and connectors to connect the sensor with the environment outside of the body.

Further scope of applicability of the present invention will become apparent from the detailed description given hereinafter. However, it should be understood that the detailed description and specific examples, while indicating preferred embodiments of the invention are given by way of illustration only. Various changes and modifications within the spirit and scope of the invention will become apparent to those skilled in the art from this detailed description.

The present invention will become more fully understood from the detailed description given herein, including the accompanying drawings which are given by way of illustration only, and thus are not limiting the present invention, and wherein.

DETAILED DESCRIPTION OF PREFERRED EMBODIMENTS

The present invention exhibits a system architecture enabling a transponder unit located within the interior of a human or animal body to communicate with electronic equipment located outside the body without the use of any signal carrying cables or physical connectors, and with reduced sensitivity to electromagnetic interference.

This is achieved with a novel principle for communicating the representation of the physiological variable to be measured, which principle also reduces the sensitivity to the precise location of the micro-sensor circuit.

In a system according to the invention, low bandwidth radio frequency power is emitted from a source outside of the subject's body, and is partially absorbed to be used as a power supply for a transponder unit, said transponder unit comprising a modulator unit and a sensor unit, disposed within the subject's body. The modulator unit is designed to alter the electromagnetic field absorption according to a pattern that is controlled by the sensor unit in response to the measured physiological variable, thereby being representative for this physiological variable. The system includes a receiver unit positioned outside of the body, which unit is effective for registering said electromagnetic field absorption.

The transponder unit according to the present invention is useful for a range of applications of invasive measurement, such as measurements within blood vessels (eg. for diagnosis of heart diseases), pressure measurements in an eye, measurement in or around the brain, aorta anoryxm measurements etc. The transponder unit could be attached to an elongated member such as a guide wire or a cannula, or could be an implantable self-containing unit.

The sensor unit of the transponder unit is not new in itself, and could include any suitable sensor device, such as a resistive sensor as described in "An IC Piezoresistive Pressure Sensor for Biomedical Instrumentation", Samann, K D Wise, J D Angell, IEEE Trans. Biomed. Eng. Vol BME-20 (1973) pp 101–109, or a capacitive sensor as described in "A Monolithic Capacitive Pressure Sensor with Pulse-Period Output", C S Sander, J W Knutti, J D Meindl, IEEE Ttans. Electron. Devices Vol. ED 27 (1980), pp 927–930.

The modulator unit of the transponder unit monitors the output from the sensor unit and provides a temporally coded modulation of the absorbed power based on the output from the sensor unit, i.e. the extent of the modulation changes in time according to a signal representing a state of the sensor. This temporal modulation, which is made according to a pre-selected algorithm, represents coded information of the physiological variable sensed by the sensor unit that is transferred into the time domain. The modulation is detected exterior of the subject's body, and as the algorithm used is known the information is easily converted to a value representing the level of the physiological variable.

Figure 1:
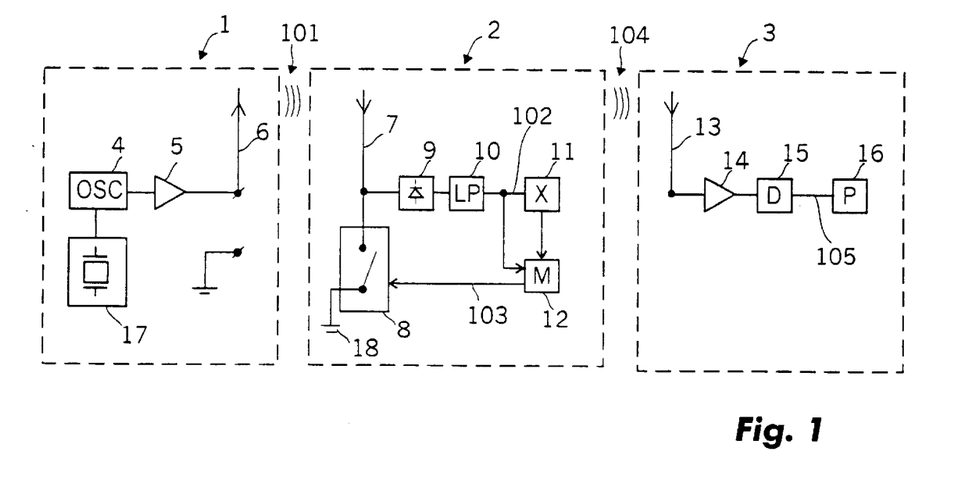
FIG. 1 is a block diagram of a first embodiment of a communication system according to the invention.

With reference to FIG. 1, an embodiment of a communication system according to the present invention includes a transmitter unit 1, a transponder unit 2 and a receiver unit 3.

The transmitter unit 1 includes a narrow-band oscillator 4, an amplifier 5 and an antenna 6. Radio frequency waves 101 of substantially constant amplitude and frequency are emitted by the antenna 6 at the operating frequency of the oscillator 4.

In order to control and maintain the oscillating frequency at a constant or controllable frequency adequate control means, such as a quartz crystal 17, is included. With a quartz crystal it is possible to ensure a frequency stability of $10^{-6}$, or better. This is of importance both for the immunity against electromagnetic interference of the system, and to avoid undesired induced interference from the system to other electronic equipment.

Figure 2:
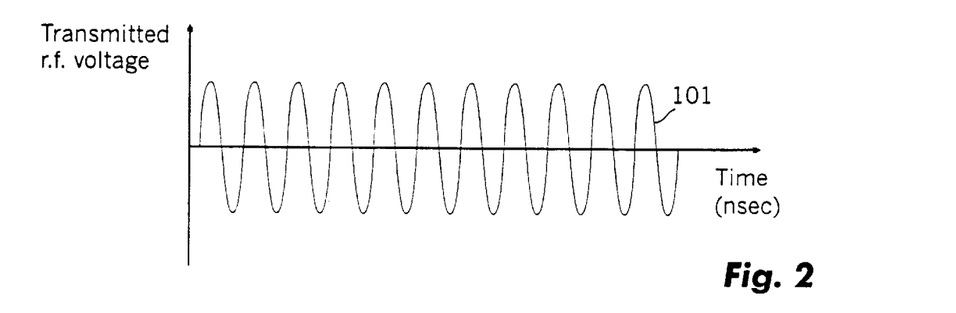
FIG. 2 is a schematical diagram of a radio frequency power transmitted from the transmitter of a communication system according to the invention.

The system is typically designed to emit radio frequency power 101 in the order of 0.1–10 W, depending on operating geometric range, accuracy requirements etc. The operating frequency may be in the range of 100 MHz–10 GHz, typically about 400 MHz. The schematical diagram of FIG. 2 illustrates, in a non-scalar way, the transmitted radio frequency voltage as a function of time.

The transponder unit 2 of FIG. 1 includes means for converting power generated by the transmitter unit 1 into a local voltage. When power is capacitively received a single wire, i.e. a transponder antenna 7, can operate as converting means, provided that a ground electrode at a potential differing from that of the transponder antenna 7 can be defined. A voltage difference between the transponder antenna and the ground electrode will arise as soon as there is a net potential gradient in the transmission medium. Therefore, a single wire, such as a section of a core wire of a guide wire, with a ground electrode can function as a converting element to electromagnetic waves, and works especially well at high frequencies corresponding to wave lengths of the same order of magnitude as the wire length.

The voltage appearing across the terminals of the antenna 7 and the neutral ground 18 is input to a rectifier 9, for example a Schottky diode in the case of a very high frequency or a pn-semiconductor in the case of a more moderate frequency.

Figure 3:
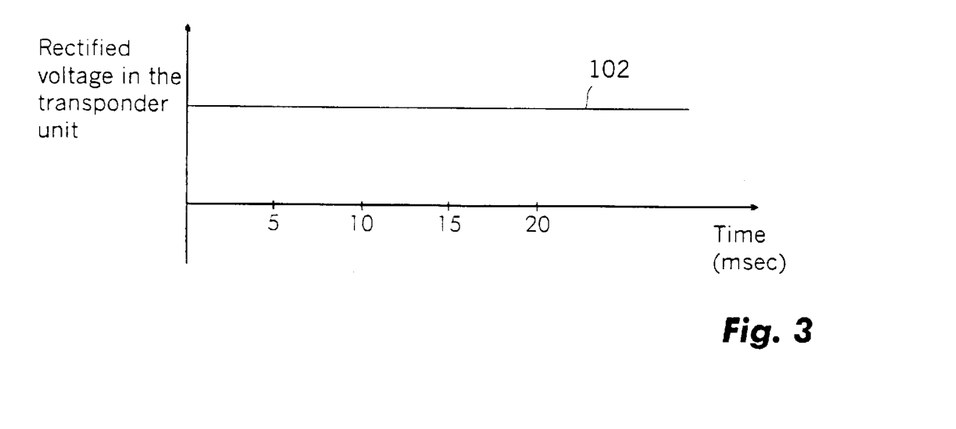
FIG. 3 is a schematical diagram of a rectified voltage in a transponder unit of a communication system according to the invention.

The rectified voltage passes through a low-pass filter 10 and then serves as a supply voltage for a micro-sensor 11 and a modulator 12. The signal 102 between the low-pass filter 10 and the micro-sensor 11 is schematically illustrated in the diagram of FIG. 3, showing the constant rectified voltage 102 as a function of time.

The micro-sensor 11 responds to the physiological variable, such as pressure, flow, temperature etc, that is to be measured and provides an output signal corresponding to the variable. It may operate on a resistive, capacitive, piezoelectric, pyroelectric or optical principle of operation, according to well-established practice of sensor design.

Figure 4:
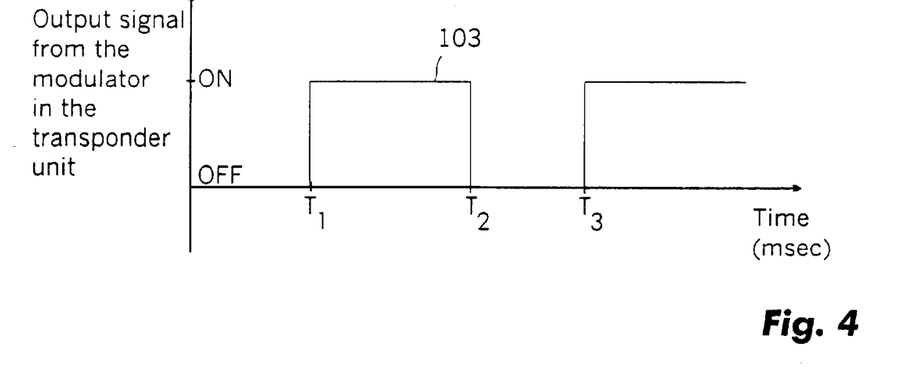
FIG. 4 is a schematical diagram of an output signal from a modulator in a transponder unit of a communication system according to the invention.

The modulator 12 converts the output signal of the micro-sensor 11 into a temporally coded signal, according to a specified scheme or algorithm, for example pulse-width modulation (PWM), frequency modulation (FM) etc. The modulation is fed back to the transponder antenna 7 via the switch 8. The output signal 103 from the modulator 12 is schematically shown in FIG. 4. As is shown in FIG. 4, the output signal is OFF up to the time T1. Between the time T1 and T2 the output signal is ON, after which it again cut OFF. At the time T3 it is again ON, and so on.

Thus, the power absorbed by the transponder unit 2 is influenced by the action of the switch 8, such that the absorption is different when the switch is in the ON state or the OFF state, respectively.

This difference in power absorption will also show as fluctuations in the electromagnetic field emanating from the transmitter unit 1 in such a way that it can be detected by a receiver unit 3. Thus, the radio frequency voltage 104 detected by the receiver unit 3 will exhibit a higher level HL during the time interval between T1 and T2, and a lower level LL before the time T1 and during the time interval between T2 and T3 etc., as is illustrated in FIG. 5.

Figure 6:
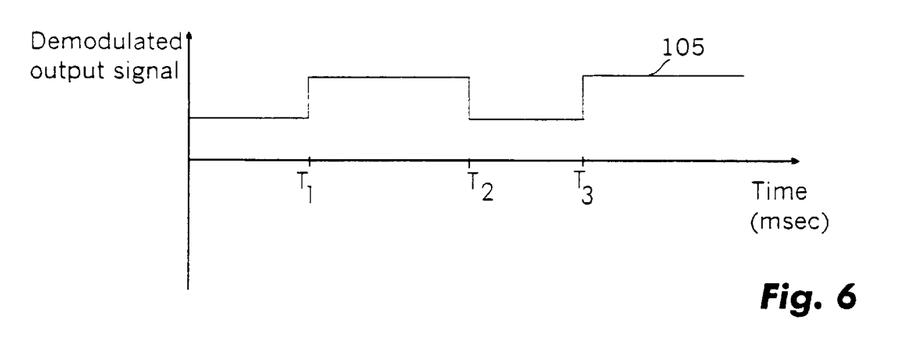
FIG. 6 is a schematical diagram of a demodulated output signal.

This enables the information of the measured variable superimposed onto the transmitted electromagnetic field to be extracted by a demodulator of the receiver unit, thereby producing a signal 105, as is seen in FIG. 6, having substantially the same temporal properties as the output signal 103 from the modulator in the transponder unit, i.e. each change from a "high" to a "low" occurs at substantially the same point in time for the signal 103 from the modulator and the signal 105 from the demodulator. Thereby, the temporal information included in the signal can be extracted.

Figure 5:
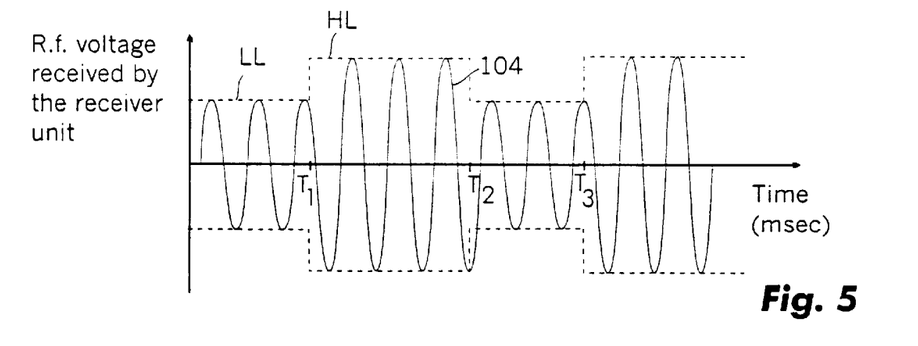
FIG. 5 is a schematical diagram of a radio frequency power received by a receiver unit of a communication system according to the invention.

It should be noted that the schematical waves of FIG. 5 are non-scalar. Typically, the transponder unit 2 absorbs 0,1–1% of the total energy radiated by the transmitter unit 1, and of this portion the range of modulation provided via the switch 8 is typically 1–10% thereof.

Any useful algorithm to transfer a measure of the physical variable to a characteristic value represented with one or several intervals of high or low absorption of the radio frequency voltage could be selected. For example, the modulator 12 could be adapted to close the switch 8 for a time interval directly proportional to the measured variable. Of course the variable could be measured repeatedly at selected intervals, each of said measurements initiating the modulator to close the switch for an appropriate length of time.

As an alternative, a measured value could be frequency coded in such a way that the modulator 12 closes the switch 8 a selected number of times for a given time interval, corresponding to a predetermined level of the measured variable.

The modulator 12 typically consists of digital logic and sequential circuitry, preferably designed by CMOS (complementary metal oxide semiconductor) technology for the purpose of low power consumption. The switch 8 may be a single transistor, either a bipolar or a field effect transistor, depending on the type of modulation, operating frequency etc.

The transponder unit 2 may be physically miniaturised into one or a few components of very small size. For example, the micro-sensor 11 may be a capacitive pressure sensor fabricated by surface machining of silicon, and having dimensions less than 100×100×100 microns. The electric circuitry, including the rectifier 9, lowpass filter 10, modulator 12 and the switch 8 may be integrated on a separate silicon die having approximately the same dimensions as the micro-sensor.

The transponder antenna 7 is preferably integrated with a core wire 51 of a guide wire structure, as will be described below with reference to FIG. 11, but could also be attached to an implant as will described below with reference to FIG. 13. Electrical connections between the components can be efficiently made by wire bonding or 'flip-chip'bonding.

The receiver 3 includes a receiver antenna 13, an amplifier 14, and a demodulator 15. The demodulator 15 converts the time or frequency coded signal back to a sensor signal, according to an inverse algorithm as that of the modulator 12. The receiver 3 also includes means for signal processing and presentation 16.

The amplifier 14 is preferably of the type known in the literature as phase-sensitive, phase-tracking, or synchronous amplifier. The bandwidth of such an amplifier can be extremely small. The system according to the invention is preferably operating at an extremely small bandwidth in order to minimise the influence of electromagnetic disturbances.

Figure 8:
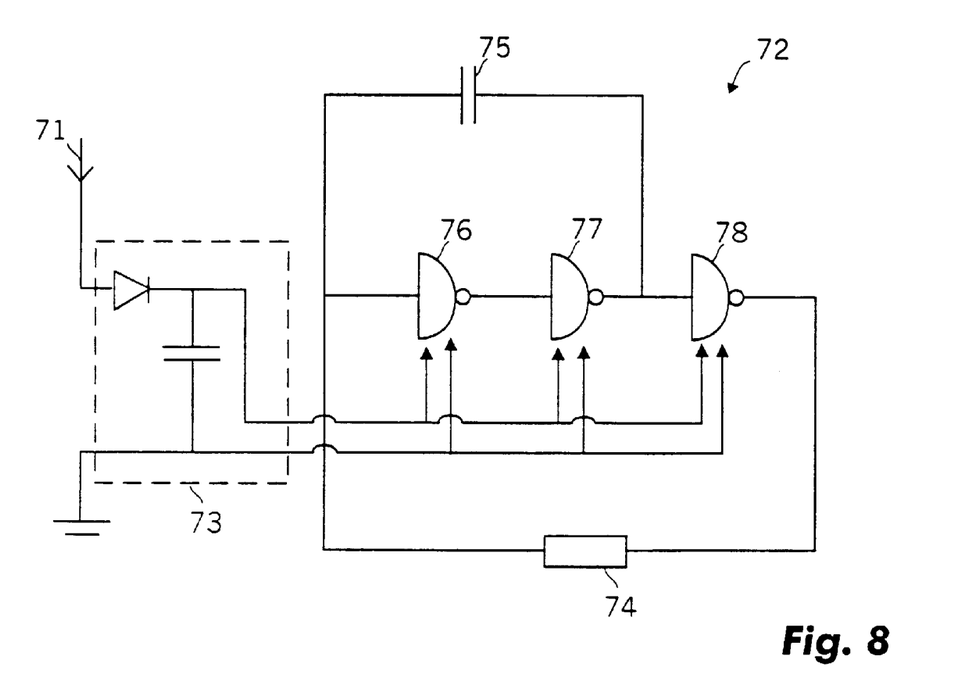
FIG. 8 is a circuit diagram of an embodiment of a transponder unit of the communication system according to the invention.

An example of a detailed circuit diagram of an embodiment of a transponder unit 72 comprising a transponder antenna 71, a rectifier 73 consisting of a diode and a capacitor, a capacitive sensor 75, three inverters 76, 77, 78, and a resistor 74 is shown in FIG. 8. The circuit forms a square wave generator operating at a period time given by R×C, where R is the resistance of the resistor 74 in ohm, and C is the capacitance of the sensor 75 in Farad. Thus, the period time will correspond to the value of the physiological variable as measured. If implemented in CMOS technology, this circuit has extremely low current consumption. In fact, the main power consumption takes place during the short switching instances. Due to this transient increase in the power consumption, these instances may be detected remotely by an external demodulator unit as will be described below.

Figure 9:
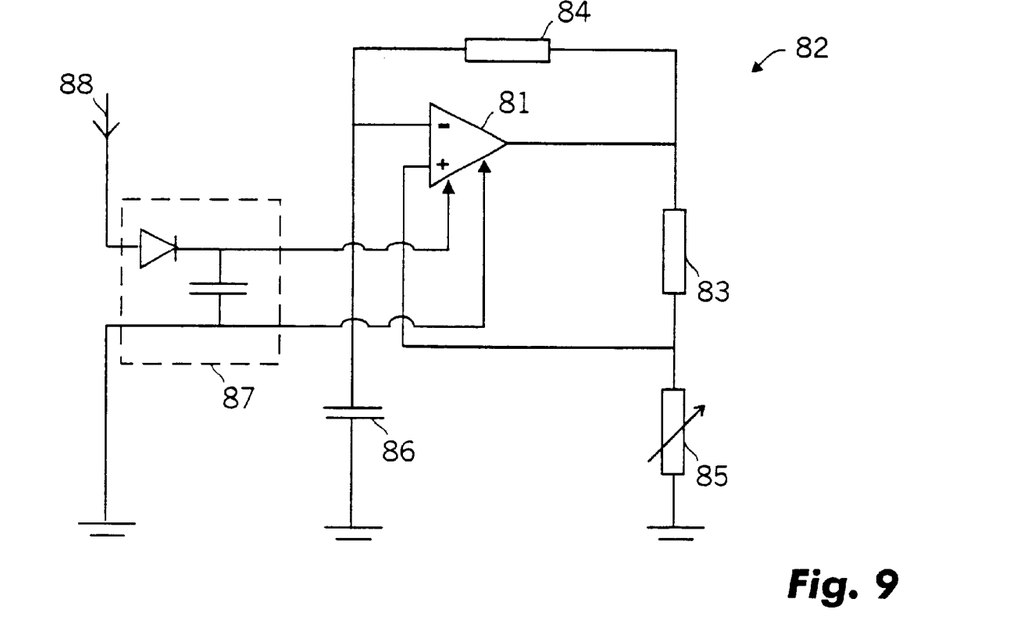
FIG. 9 is a circuit diagram of another embodiment of a transponder unit of the communication system according to the invention.

In FIG. 9 is shown a detailed circuit diagram of yet another embodiment of a transponder unit 82, comprising a resistive sensor 85, a rectifier 87 consisting of a diode and a capacitor, an operational amplifier 81, two other resistors 83, 84, a capacitor 86 and a transponder antenna 88. Analogous to the circuit described above with reference to FIG. 8, the circuit on FIG. 9 generates a square wave, the period of which is determined by the passive components of the circuit, e.g. the resistance of the sensor 85.

Figure 7:
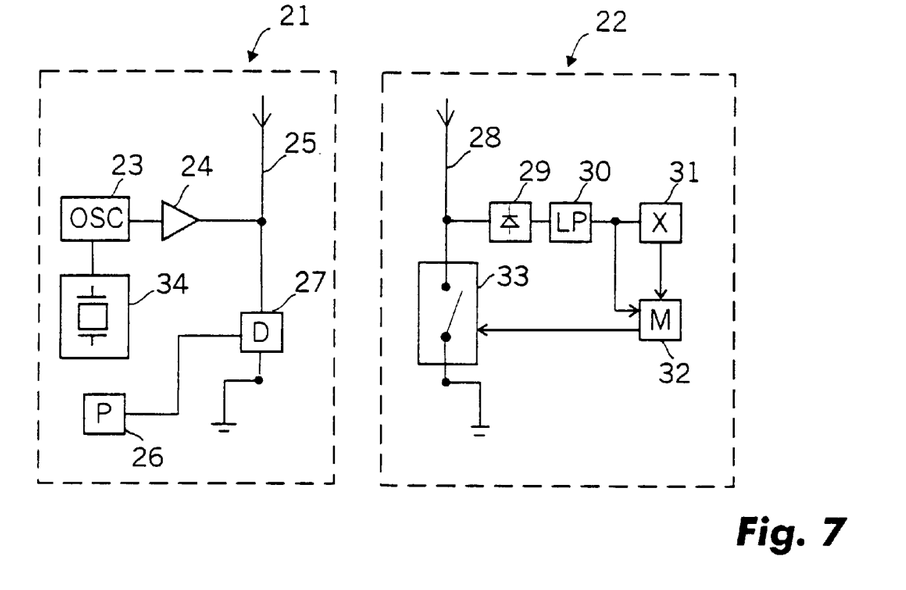
FIG. 7 is a block diagram of a second embodiment of a communication system according to the invention.

In FIG. 7 is shown a second embodiment of the communication system according to the invention. The transponder unit 22 corresponds to the transponder unit 2 of FIG. 1, and includes a transponder antenna 28, rectifier 29, low-pass filter 30, microsensor 31, modulator 32, and switch 33.

The transceiver unit 21 of FIG. 7 operates both as a transmitter of radio frequency power, and as a receiver of the sensor signal provided as a passive modulation of the power absorbed by a transponder unit 22. Thus, the transceiver unit 21 includes an oscillator 23, a quartz crystal 34, an amplifier 24, and an antenna 25 analogous to the transmitter unit 1 of FIG. 1. In addition, the transceiver unit 21 also includes a demodulator 27, and means for signal processing and presentation 26, analogous to the receiver unit 3 of FIG. 1.

The demodulator 27 is used to detect small and time dependent variations of the antenna 25 impedance. When there is a variation of the power absorption induced by the modulator 32 and the switch 33, variations of the antenna impedance will be induced according to well-established principles of reciprocal networks.

Figure 10:
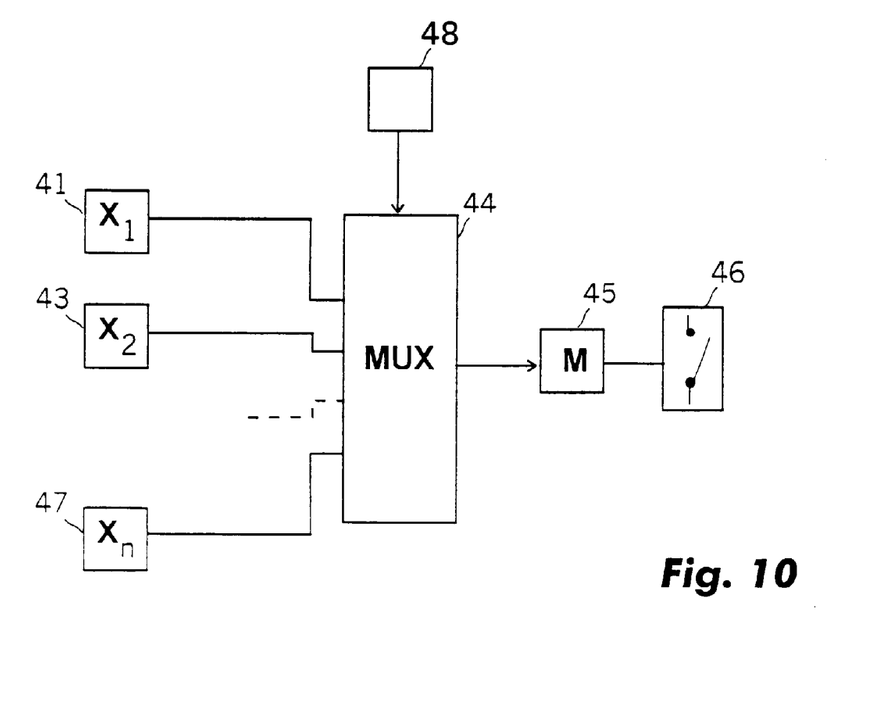
FIG. 10 is a block diagram of an embodiment of transponder unit of a communication system according to the invention providing the possibility to sequentially measure and transmit several physiological variables.

With reference to FIG. 10, an embodiment of a transponder unit 42 in a communication system according to the present invention providing the possibility to sequentially measure and transmit several physiological variables is illustrated. Although not shown in FIG. 10, a transmitter unit and a receiver unit corresponding to what is described with reference to FIG. 1, or a transceiver as is described with reference to FIG. 7, is also included in the communication system.

A selected number of microsensors 41, 43, 47 (three being shown as an example in FIG. 10, and additional microsensors being suggested by a dotted line), each one responding to one or several of the physiological variables to be studied, are provided.

Each sensor 41, 43, 47 provides a signal representative of at least one physiological variable to a multiplexer 44 which sequentially or according to some other predetermined rule connects each sensor to a modulator 45 and a switch 46. The operational principle of the modulator 45 and the switch 46 is analogous to the previously described modulator 12 and switch 8 of FIG. 1. The sequence in which individual sensors 41, 43, 47 are connected to the modulator 45 may either be based on a free-running oscillator (not shown) included in the modulator and sensor unit 42, or be triggered by an addressing routine embedded in the power emission from the transmitter unit, e.g. by frequency or amplitude modulation of the power emission. Thus, many configurations are possible for controlling the transmission of a monitored value from a sensor, but common to all such configurations is that a microcontroller 48 is connected to the multiplexer 44 to provide digital control of the addressing routines.

Figure 11:
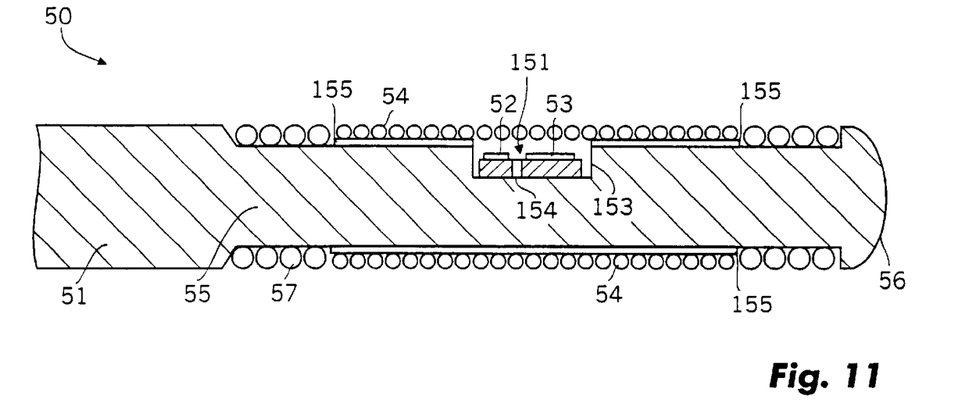
FIG. 11 is a cross sectional view of the distal end of a guide wire with a transponder unit.

With reference to FIG. 11, a transponder unit 151, including a microsensor 52 and a power converting and modulating circuit 53 as described above is mounted at the distal end of a guide wire 50 is shown. A core wire 51 extends through the length of the guide wire. The core wire 51, which may consist of a single or multi-strand wire, is typically provided with a section 55 having a reduced diameter to ensure a reduced bending stiffness to reduce the risk of rupturing the vessel during positioning. For the same reason, the guide wire tip 56 is typically rounded. A coil 57 covers the section 55 of reduced diameter to provide the distal end of the guide wire with a substantially uniform outer diameter.

The transponder unit 151 is mounted in a recess 153 in the core wire section 55, and is electrically connected 154 to the core wire 51 in order to provide a ground potential to the transponder unit via the core wire.

A coil wire section 54 of a radio opaque material such as platinum is helically wound around a part of the guide wire section 55 to cover the transponder unit 151 and, at the same time, to form a part of the guide wire distal end outer surface, similarly to the coil 57. The coil wire 54 is insulated from the core wire 51 by an insulating layer 155, and is connected to the transponder unit to act as a power converting means, such as is described with reference to the power converting transponder antenna 7 of FIG. 1.

Thus, since the core wire 51 and the wire 54 have different locations in space a voltage will occur between them when an electrical field gradient is present, as is the case when a transmitting or transceiver unit as described above is activated.

Figure 12:
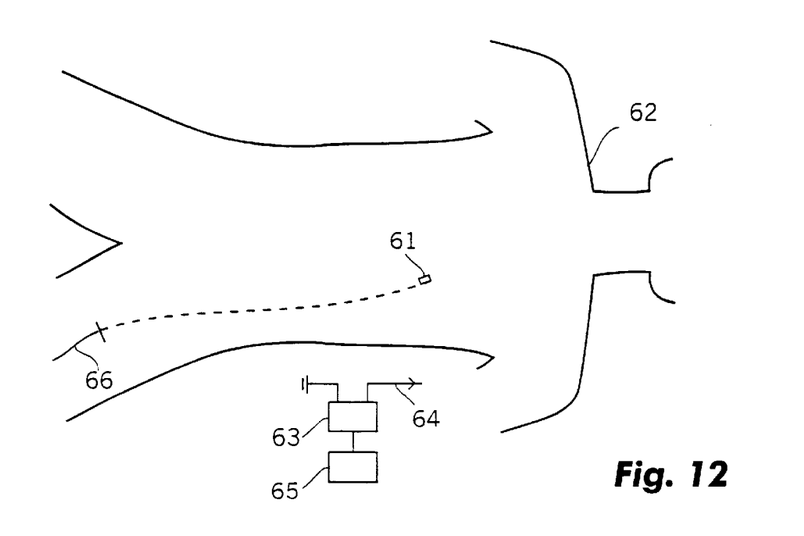
FIG. 12 is a schematical sketch of a system according to the present invention in use.

FIG. 12 illustrates an example of use of a system according to the present invention, wherein a subject 62 is investigated with a transponder unit 61 that is mounted on a guide wire 66. The guide wire 66 has been surgically inserted into the femoral artery and has been advanced until the transponder unit 61 is located within the heart, making local cardiovascular measurements possible. Exterior to the subject 62 is placed a transceiver unit 63 with an antenna 64. The transceiver unit 63 is connected to a signal processing and presentation unit 65. The signal processing and presentation unit 65 could be any proper multipurpose device, such as a personal computer with a suitable interface circuit, as is apparent for anyone skilled in the art.

Figure 13:
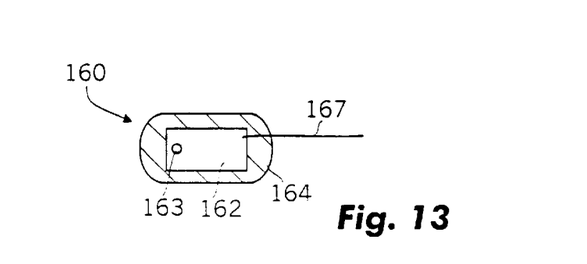
FIG. 13 is a schematic cross sectional view of an implant according to the present invention.

Instead of being mounted onto a guide wire, the transponder unit could be mounted on a substrate 162 to be inserted into the body as an implant 160, as shown in FIG. 13. The implant is covered with an protective encapsulating material 164, such as a silicon resin, to protect the circuitry as well as the body tissue surrounding the implant. A transponder antenna 167 connected to the transponder unit, as described above for the different embodiments of transponder antenna, and made from a biologically acceptable metal passes through the encapsulating material.

Of course, the transponder unit of a substrate, including its sensor, could for example be anyone of those previously described herein.

The implant 160 is disposed at the site of measurement and is fastened thereto by a suitable attachment means of the implant. An example of such an attachment means is shown in FIG. 13 as hole 163 through the implant, which hole is used for anchoring the implant with a suture. Other such attachment means could be clamps or hook-like protrusions.

Thus, according to the present invention, the information of the physiological variable is determined using a constant pre-selected carrier frequency, as opposed to the previously used systems wherein a frequency sweep is used to determine a resonance frequency, the value of which is indicative of the physiological variable. Instead, the information is superimposed on the constant carrier frequency in the form of a time or frequency based modulation.

According to the invention, the carrier frequency is provided to the transponder unit disposed in a living body by an alternating electromagnetic field that also provides energy for operating the transponder unit. The transponder unit interacts with the electromagnetic field applied in a way that is determined by at least one physical parameter at the site of the sensor. The interaction, being observable as a change in the electromagnetic field strength according to a pattern representing a value of the physical parameter, is monitored outside of the body and is interpreted by a demodulating unit.

Thus, the communication of the measured parameter value is achieved in a wireless manner, therefore eliminating the need for connectors and wires along the guide wire.

With the invention a number of advantages are obtained.

Thus, the required electronic circuitry may be integrated on a single silicon die, having extremely small dimensions, and requires only a small number of discrete components. In all, all necessary components can be accommodated and packaged within the available space of a guide wire having an outside diameter of 0.4 mm or less.

Also, the system operates at a low bandwidth, and is hence not sensitive to electromagnetic disturbances. Furthermore, it is not sensitive to the position of the transmitter or to the precise control of the transmission properties of the medium.

It is obvious that the present invention may be varied in many ways with respect to the detailed description above. Such variations are not to be regarded as a departure from the spirit and scope of the invention, and all such modifications as would be obvious to one skilled in the art are intended to be included within the scope of the following claims.

What is claimed is:

1. A biotelemetry system for measuring a physiological variable within a living body, including a radio frequency transmitter to be disposed outside of the body, a radio frequency energy receiver to be disposed outside of the body, and a transponder unit including a sensor sensitive to the physiological variable, wherein the transponder unit is characterised by a modulator unit for controlling radio frequency energy absorption of the transponder unit according to a time-sequence representing said physiological variable, the transponder unit being disposed on a guide wire.

2. The biotelemetry system according to claim 1, wherein the transponder unit comprises a transponder antenna and a rectifier, said antenna and rectifier forming a power supply for the sensor and the modulator unit.

3. The biotelemetry system according to claim 2, wherein at least a part of said antenna is integrated with a core wire of the guide wire.

4. The biotelemetry system according to claim 1, wherein the transponder unit comprises a resistive sensor.

5. The biotelemetry system according to claim 1, wherein the transponder unit comprises a capacitive sensor.

6. The biotelemetry system according to claim 1, wherein the transponder unit comprises a transponder antenna, a rectifier, a capacitive sensor, inverters, and a resistor.

7. The biotelemetry system according to claim 1, wherein the transponder unit comprises a resistive sensor, a rectifier, an operational amplifier, resistors, a capacitor; and a transponder antenna.

8. The biotelemetry system according to claim 1, wherein the transmitter includes a narrow-band oscillator for providing a substantially constant output frequency and amplitude, and the receiver includes a narrow-band amplifier operating at the same frequency as the transmitter.

9. The biotelemetry system according to claim 8, wherein said narrow-band amplifier is a synchronous amplifier.

10. A guide wire, having a transponder unit disposed at one end wherein the transponder unit comprises:

a sensor sensitive to a physiological variable; and a modulator unit for controlling radio frequency energy absorption of the transponder unit according to a time-sequence representing said physiological variable.

11. The guide wire according to claim 10, wherein the transponder unit comprises a transponder antenna and a rectifier, said antenna and rectifier forming a power supply for the sensor and the modulator unit.

12. The guide wire according to claim 11, wherein at least a part of said antenna is integrated with a core wire of the guide wire.

13. The guide wire according to claim 10, wherein the transponder unit comprises a resistive sensor.

14. The guide wire according to claim 10, wherein the transponder unit comprises a capacitive sensor.

15. The guide wire according to claim 10, wherein the transponder unit comprises a transponder antenna, a rectifier, a capacitive sensor, inverters, and a resistor.

16. The guide wire according to claim 10, wherein the transponder unit comprises a resistive sensor, a rectifier, an operational amplifier, resistors, a capacitor; and a transponder antenna.

17. A method for measuring a physiological variable in a living body, wherein a transmitter is disposed outside of the body to transmit radio frequency energy, and a receiver of radio frequency energy is disposed outside of the body, the method comprising the steps of:

introducing a guide wire on which is disposed a transponder unit having a sensor sensitive to the physiological variable, and a modulator unit for controlling radio frequency energy absorption of the transponder unit according to a time-sequence representing said physiological variable;

operating the transmitter to provide the transponder unit with a radio frequency energy of substantially constant frequency and amplitude;

operating the receiver to monitor the radio energy absorption of the transponder unit to determine the time-sequence representing said physiological variable; and decoding said absorption time-sequence to interpret said absorption time-sequence as a measure of the physiological variable.

18. The method according to claim 17, further comprising introducing said guide wire into a vessel of the body, wherein said sensor and modulator unit are disposed at a distal end of said guide wire.

* * * * *

UNITED STATES PATENT AND TRADEMARK OFFICE
CERTIFICATE OF CORRECTION

PATENT NO. : 6,692,446 B2
DATED : February 17, 2004
INVENTOR(S) : Bertil Hoek It is certified that error appears in the above-identified patent and that said Letters Patent is hereby corrected as shown below:

<u>Title page,</u>
Item [*] Notice, should read -- Subject to any disclaimer, the term of this patent is extended or adjusted under 35 U.S.C. 154(b) by 61 days. --

Signed and Sealed this

Thirteenth Day of April, 2004

JON W. DUDAS
*Acting Director of the United States Patent and Trademark Office*